United States Patent [19]

Nutt

[11] 4,304,724

[45] Dec. 8, 1981

[54] PROCESS FOR THE MANUFACTURE OF ANTHRAQUINONE

[75] Inventor: Michael O. Nutt, Baton Rouge, La.

[73] Assignee: The Dow Chemical Company, Midland, Mich.

[21] Appl. No.: 219,292

[22] Filed: Dec. 22, 1980

[51] Int. Cl.$^3$ .................. C07C 50/18; B01J 31/02; C07C 2/02; C07C 5/22

[52] U.S. Cl. .................. 260/369; 252/426; 252/428; 585/332; 585/375; 585/470; 585/730; 585/749

[58] Field of Search .............. 252/426, 428; 585/332, 585/375, 470, 730, 749; 260/369

[56] References Cited

U.S. PATENT DOCUMENTS

| | | | |
|---|---|---|---|
| 3,326,809 | 6/1967 | Mageli et al. | 252/426 |
| 3,408,349 | 10/1968 | Matsunaga | 252/426 |
| 4,038,213 | 7/1977 | McClure et al. | 252/430 |
| 4,045,456 | 8/1977 | Merger et al. | 260/369 |
| 4,054,683 | 10/1977 | Gruber | 252/426 |

OTHER PUBLICATIONS

*Chemical Abstracts,* vol. 80, #133126u, "Anthraquinone" Japan, Kokai, 74,07,260, 1974.

*Primary Examiner*—Winston A. Douglas
*Assistant Examiner*—Raymond K. Covington
*Attorney, Agent, or Firm*—Arthur J. Young

[57] ABSTRACT

The present invention provides a process for making anthraquinone by the cyclization reaction of orthobenzoylbenzoic acid. The process uses as a catalyst a cation-exchange resin formed from a polymer with a polytetrafluoroethylene backbone and sulfonic-acid sidechains.

7 Claims, No Drawings

PROCESS FOR THE MANUFACTURE OF ANTHRAQUINONE

BACKGROUND OF THE INVENTION

The present invention relates to the manufacture of anthraquinone. More particularly, the invention relates to a catalyst which is particularly useful for cyclizing ortho-benzoylbenzoic acid to anthraquinone.

It is known that a perfluorinated sulfonic-acid resin can be used as a catalyst for the conversion of hydrocarbons to other hydrocarbons, see U.S. Pat. No. 4,038,213. Examples of the reactions include alkylation of isoparaffins, isomerization of normal alkanes, disproportionation of toluene and alkylation of benzene. In addition, U.S. Pat. No. 4,045,456 describes a process for cyclizing ortho-benzoylbenzoic acids to the corresponding anthraquinones in the presence of oxygen-containing compounds of aluminum and silicon at elevated temperatures (150°–400° C.), and Japanese Kokai No. 74/07, 260 teaches the preparation of anthraquinone by heating ortho-benzoylbenzoic acid with 0.01 to 0.2 parts of concentrated sulfuric acid in the molten state, followed by sublimation in vacuo at 300°–350° C.

SUMMARY

In general, this invention provides for the manufacture of anthraquinone, comprising the step of contacting a solution of ortho-benzoylbenzoic acid in an inert solvent with a perfluorinated cation-exchange resin, in the acid form, as a catalyst at a temperature of between about 100° C. and about 200° C. The reaction may be carried out on a batch or continuous basis and the anthraquinone product may be recovered by well-known means such as evaporation, or cooling and crystalization followed by filtration.

It is an object of this invention to provide a process for the manufacture of anthraquinone. It is a further object of this invention to provide a catalyst therefor which is characterized as being heterogeneous and easily separated from the reaction-product mixture. It is a further object of this invention to provide a catalyst therefor which is useful for a prolonged period of time under batch or continuous reaction conditions. Other objects of the invention will be apparent to those skilled in the art from the more detailed description which follows.

DESCRIPTION OF THE PREFERRED EMBODIMENTS

The following description illustrates the manner in which the principles of the present invention are applied, but is not to be construed as in any sense limiting the scope of the invention.

More specifically, ortho-benzoylbenzoic acid is dissolved in an inert solvent to form a solution which preferably has a concentration of between about thirteen and about twenty-three percent by weight acid and, more preferably, between about sixteen and twenty-one percent by weight acid. The preferred solvent for carrying out the cyclization reaction is ortho-dichlorobenzene.

The solution is then heated to between about 100° C. and about 200° C., preferably between about 120° C. and about 180° C., more preferably between about 140° C. and about 160° C., and most preferably between about 145° C. and about 155° C., and contacted with a perfluorinated cation-exchange resin, in the acid form, which catalizes the cyclization reaction of the ortho-benzoylbenzoic acid to anthraquinone.

The cation-exchange resin, which acts as a catalyst for the reaction, is preferably formed from a polymer with sulfonic-acid sidechains. More preferably, the resin is formed from a polymer with a polytetrafluoroethylene backbone and sulfonic-acid sidechains. Such a resin is manufactured and sold by E. I. DuPont de Nemours and Company, Inc., under the registered trademark NAFION[R].

The anthraquinone product may be recovered by cooling the reaction mixture, whereupon the anthraquinone crystallizes out of solution and may be separated from the mother liquor by filtration.

The present invention is further illustrated by means of the following example, which is illustrative only and is not to be construed as in any sense limiting the scope of the invention.

EXAMPLE 1

Three grams (13.3 millimoles) of ortho-benzoylbenzoic acid in thriteen grams of ortho-dichlorobenzene was contacted and stirred for three hours at 150° C. with a cation-exchange resin formed from a polymer with a polytetrafluorethylene backbone and sulfonic-acid sidechains. The specific resin used was purchased from E. I. DuPont de Nemours and Company, Inc. under the tradename NAFION[R]. Analysis of the reaction-product mixture showed that 1.2 grams (5.31 millimoles) of ortho-benzoylbenzoic acid remained unreacted, and that 1.3 grams (6.25 millimoles) of anthraquinone had been formed. These date indicate a conversion of sixty percent, with seventy-eight percent selectivity to anthraquinone.

While certain representative embodiments and details have been shown for the purpose of illustrating this invention, it will be apparent to those skilled in the art that various changes and modifications can be made therein without departing from the spirit and scope of the invention.

What is claimed is:

1. A process for making of anthraquinone, comprising the step of contacting a solution of ortho-benzoylbenzoic acid in an inert solvent with a perfluorinated cation-exchange resin, in the acid form, at a temperature of between about 100° C. and about 200° C.

2. The process of claim 1, wherein the resin is formed from a polymer with sulfonic-acid sidechains.

3. The process of claim 2, wherein the resin is formed from a polymer with a polytetrafluoroethylene backbone.

4. The process of claim 3, wherein the solvent is ortho-dichlorobenzene.

5. The process of claim 4, wherein the temperature is between about 120° C. and about 180° C.

6. The process of claim 5, wherein the temperature is between about 140° C. and about 160° C.

7. The process of claim 6, wherein the temperature is between about 145° C. and about 155° C.

* * * * *